United States Patent [19]

Burt

[11] 4,070,247

[45] Jan. 24, 1978

[54] DIAGNOSTIC MEDIA

[75] Inventor: Stanton C. Burt, Indianapolis, Ind.

[73] Assignee: Indiana University Foundation, Bloomington, Ind.

[21] Appl. No.: 782,612

[22] Filed: Mar. 30, 1977

[51] Int. Cl.$^2$ .............................................. C12K 1/04
[52] U.S. Cl. ............................. 195/100; 195/103.5 M
[58] Field of Search ................. 195/103.5 M, 100, 102

[56] References Cited

U.S. PATENT DOCUMENTS

| 3,870,601 | 3/1975 | Warren et al. | 195/103.5 M |
|---|---|---|---|
| 3,957,584 | 5/1976 | Kronish et al. | 195/103.5 M |

*Primary Examiner*—Alvin E. Tanenholtz

[57] ABSTRACT

Improved diagnostic media for isolating, identifying, and classifying *Enterobacteriaceae* comprise an effective amount of isopropyl-beta-D-thiogalactopyranoside in order to reduce the incidence of false lactose negative determinations and to differentiate between lac inducible and lac constitutive bacteria.

9 Claims, No Drawings

DIAGNOSTIC MEDIA

BACKGROUND OF THE INVENTION

1. Field of the Invention

This invention relates to the microbiological arts and more particularly to improved diagnostic media for use in isolating, identifying, and classifying Enterobacteriaceae.

2. Description of the Prior Art

In the course of metabolizing lactose, E. coli must make two proteins, the first of which, galactoside permease (also known as lactose permease), is responsible for transporting lactose through the bacterial cell envelope and thus permits the accumulation of the substrate lactose within the cell. The second essential protein is betagalactosidase, which cleaves the disaccharide lactose into the monosaccharides glucose and galactose, which are further metabolized.

When grown in the absence of lactose, the normal E. coli cell produces only basal (extremely low) levels of galactoside permease and beta-galactosidase. However, in the presence of lactose, the cells increase synthesis of these two proteins by one hundred to a thousand times. The "induction" of these two proteins in the presence of lactose is thus a critical step in the cell's ability to ferment lactose. Those lactose positive Enterobacteriaceae that lack the regulatory genes necessary for this "induction" and therefore always produce high levels of beta-galactosidase and galactoside permease are called constitutive. The lac operon of E. coli codes for the structural and regulatory genes described above that are responsible for the metabolism of lactose.

The fermentation of lactose (glucose-4-beta-galactoside) resulting in the production of acid and gas has long been a characteristic used in identifying the Enterobacteriaceae. In particular, lactose fermentation is a major characteristic employed in the identification of species such as E. Coli by bacterial taxonomists, water bacteriologists, and, especially, clinical microbiologists.

All three groups of bacteriologists have employed standard media to differentiate between lactose fermenters and non-lactose fermenters as this trait became the major biochemical test in dividing the Enterobacteriaceae into its component members. While such media differ depending upon the particular purpose to which they are put, in general, they have as their characteristic feature the presence of a lactose substrate upon which the microorganism could act coupled with other conventional nutrient carriers such as agar.

With particular reference to clinical microbiologists and their task of identifying various microbes in specimens presented for analysis, the major objective is to differentiate quickly yet reliably between pathogens, which may be the cause of a particular problem, and a patient's normal bacterial flora. Identification and differentiation of Enterobacteriaceae, which include both pathogens and non pathogenic bacteria usually found to be normal flora, rely mainly on an array of biochemical tests. The ability or inability of a particular microorganism to ferment lactose in triple sugar iron (TSI) agar or other indicator media containing lactose is the single most valuable biochemical tool used in distinguishing one member of the Enterobacteriaceae from another. In particular, lactose positiveness is a major aid in distinguishing non pathogenic E. coli from Salmonella and Shigella, the latter pathogens which are for the most part lactose negative.

A significant problem encountered by the clinical microbiologist is that approximately ten percent of all E. coli appear to be lactose negative. When a lactose negative Enterobacteriaceae is found, extensive biochemical tests must be run to assure that the microbe is not Salmonella or Shigella. Thus, much additional work must be undertaken, and delay arises before the proper identification can be made and treatment for the patient prescribed. Thus, the value and validity of the lactose test is materially reduced by the prevalence of lactose negative E. coli.

Accordingly, a primary object of this invention is to develop an improved basis for distinguishing between lactose positive and lactose negative Enterobacteriaceae.

Another object is to provide improved diagnostic media, the use of which significantly reduces the incidence of false lactose negative determinations of E. coli.

A still further object is to provide an improved method for distinguishing between those lactose positive Enterobacteriaceae that produce enzymes of the lac operon constitutively and those inducible strains that have the regulatory genes typical of E. coli.

A SUMMARY OF THE INVENTION

The foregoing and other objects, advantages, and features of this invention may be obtained by incorporating in suitable nutrient containing media a minor but effective amount of isopropyl-beta-D-thiogalactopyranoside (hereinafter referred to as "IPTG").

It has been found that 95% of lactose negative strains of E. coli having otherwise typical E. coli reactions in Triple Sugar Iron Agar, SIM Medium, and Simmons Citrate Agar have the capacity to make beta-galactosidase when induced with IPTG. These strains have been shown to be lactose negative because they lack galactoside permease activity. Without basal levels of galactoside permease activity thse cells do not concentrate enough lactose inside the cell to induce the lac operon and therefore only 1/100 to 1/1000 of the induced level of beta-galactosidase is produced even in a lactose containing medium. IPTG at a level of as little as about 0.0024% by weight will induce the production of beta galactosidase when lactose cannot.

A second purpose for incorporating IPTG into diagnostic media is to differentiate between strains that have an inducible system for the production of beta-galactosidase and those that have constitutive synthesis of that enzyme. It is believed that many Enterobacteriaceae able to ferment lactose do not have the regulatory genes possessed by E. coli and therefore produce beta-galactosidase constitutively. By comparing the beta-galactosidase assays of cells grown in the presence of IPTG with those grown in the absence of any inducer it can be determined whether that strain is inducible or constitutive with respect to the lac operon.

Thus, in its method aspect, this invention involves a method for classifying microorganisms comprising the steps of inoculating the microorganism onto a diagnostic medium comprising at least one nutrient and a minor but effective amount of isopropyl-beta-D-thiogalactopyranoside, incubating the inoculated medium; and assaying the inoculated medium for beta-galactosidase. Preferably, the assay is performed by measuring the degree to which the inoculated medium hydrolyzes ortho-nitrophenyl-beta-D-galacto-pyranoside.

DETAILED DESCRIPTION OF THE PREFERRED EMBODIMENTS

In accordance with this invention, diagnostic media used for identifying microorganisms of the Enterobacteriaceae family desirably have incorporated therein a minor but effective amount of isopropyl-beta-D-thiogalacto-pyranoside ("IPTG"). Such media, which are in all other respects a conventional, perferably contain at least about 0.0024% and preferably between about 0.0024–0.01% IPTG, by weight. Such media may include other constituents including compounds required for the growth of bacteria. Such media typically contain nutrients such as agar, saccharides (e.g. lactose, dextrose, etc.), protein sources (beef extracts, and the like), minerals (e.g. sodium chloride, ferrous sulfate, sodium phosphate), and other conventional nutritive additives. Such media may also contain color indicators as is known to those skilled in the art. An especially desirable medium to which IPTG may be added is Brom Cresol medium containing the color indicator brom cresol purple which undergoes color change in response to slight pH changes.

The assay for beta-galactosidease may be performed in substantially any suitable manner, as is known to the art. One useful technique is based on the hydrolysis of ortho-nitrophenyl-beta-D-galacto-pyranoside (ONPG) by beta-galactosidease.

The following example illustrates the composition of Triple Sugar Iron Agar to which IPTG has been added in accordance with this invention.

EXAMPLE I

| Constituent | Grams/Liter | % (by weight) |
|---|---|---|
| IPTG | .024 g. | 0.0024% |
| Beef Extract | 3 g. | 0.3% |
| Yeast Extract | 3 g. | 0.3% |
| Peptone | 15 g. | 1.5% |
| Proteose Peptone | 5 g. | 0.5% |
| Lactose | 10 g. | 1.0% |
| Saccharose | 10 g. | 1.0% |
| Dextrose | 1 g. | 0.1% |
| Ferrous Sulfate | 0.2 g. | 0.02% |
| Sodium Chloride | 5 g. | 0.5% |
| Sodium Thiosulfate | 0.3 g. | 0.03% |
| Agar | 12 g. | 1.2% |
| Phenol Red | 0.024 g. | 0.0024% |

The following examples respectively illustrate liquid and solid fermentation media to which IPTG has been added pursuant to this invention.

EXAMPLE II

| | | |
|---|---|---|
| IPTG | 0.024 g. | 0.0024% |
| Beef Extract | 1 g. | 0.1% |
| Proteose Peptone | 10 g. | 1.0% |
| Sodium Chloride | 5 g. | 0.5% |
| Lactose | 10 g. | 1.0% |
| Indicator such as Brom Cresol Purple | 0.015 g. | 0.0015% |

EXAMPLE III

| | | |
|---|---|---|
| IPTG | 0.024 g. | 0.0024% |
| Beef Extract | 1 g. | 0.1% |
| Proteose Peptone | 10 g. | 1.0% |
| Sodium Chloride | 5 g. | 0.5% |
| Agar | 15 g. | 1.5% |
| Lactose | 10 g. | 1.0% |
| Indicator such as Brom Cresol Purple | 0.02 g. | 0.002% |

Utilization of improved diagnostic media in accordance with the teachings of this invention is illustrated in the following examples:

EXAMPLE IV

Beta-galactosidase test performed on cells scraped from Triple Sugar Iron Agar (TSI) slant containing IPTG.

The procedure for the clinical assay of beta-galactosidase as described in the *Manual of Clinical Microbiology* dictates that cells are to be scraped from a TSI slant, resuspended, and tested with ortho-nitrophenyl-beta-D-galactopyranoside (ONPG) for the presence of beta-galactosidase. This assay relies upon the lactose in the TSI medium to induce the production of beta-galactosidase. By using the TSI agar of Example I which contains IPTG (0.0024% by weight), beta-galactosidease formation is induced in those cells lacking galactoside permease activity (which compose the vast majority of lactose negative *E. coli*) that otherwise give a negative beta-galactosidase reaction when tested with ONPG.

EXAMPLE V

Indicator dye layered on TSI agar slant containing IPTG.

Although beta-galactosidase positive, galactoside permease negative *E. coli* produce more acid from lactose in the presence of IPTG than in its absence, sufficient acid is not produced to affect the particular indicator dye used in TSI agar. However, after growth on the TSI medium of Example I, when a liquid is added which contains an indicator dye that exploits the difference in acidity between a true lactose negative strain and a strain capable of making beta-galactosidase when induced with IPTG, one differentiates between the two.

EXAMPLE VI

Addition of IPTG to liquid tube fermentation tests.

A liquid broth base containing the carbohydrate of interest and a dye indicator to detect the production of acid by fermentation of the carbohydrate is a common method for determining a bacterial strain's ability to metabolize a number of sugars. Beta-galactosidase positive, galactoside permease negative strains produce more acid in the presence of IPTG and lactose than in the presence of lactose alone. In a broth base medium containing at least 0.0024% IPTG and the proper indicator dye (e.g, the medium of Example II), strains that have beta-galactosidase but lack permease activity are differentiated from true lactose negative organisms. Since many of the strains designated as lactose negative ferment lactose in liquid media upon prolonged incubation (e.g., greater than 48 hours), the incorporation of IPTG into media allows such "slow lactose fermentors" to be distinguished from true lactose negative organisms in far shorter periods of time, with resulting benefits in early clinical diagnosis. Alternatively, IPTG may be incorporated into a solid fermentation medium (e.g., Example III) rather than in a liquid medium.

EXAMPLE VII

Beta-galactosidase or ONPG test on a liquid growth medium containing IPTG.

Cells are grown in the presence of IPTG and tested for beta-galactosidase production by the addition of ONPG. Tests of this type may be conducted on a miniaturized basis using small amounts (e.g., 2 ml.) of IPTG containing media and commercially available discs of ONPG.

EXAMPLE VIII

Inducible/constitutive test.

Many organisms other than *E. coli* that ferment lactose are not believed to have the regulatory genes required to produce large amounts of beta-galactosidase only in the presence of an inducer of the lac operon and produce very low levels of that enzyme in the absence of an inducer. IPTG may be used to exploit this difference as an additional characteristic in identifying members of the Enterobacteriaceae.

Bacteria are grown in two media, one containing 0.0024% IPTG and one without an inducer of the lac operon. A strain constitutive for beta-galactosidase production gives positive results when tested with ONPG in both media. Where only the IPTG containing medium is positive, the inoculated organism was inducible and thus possessed the regulatory genes typical of *E. coli*.

EXPERIMENTAL EVALUATIONS

The following experimental work demonstrates the effectiveness of the use of IPTG as an additive to diagnostic media for lactose positiveness determinations. For purposes of this study, *Escherichia coli* was determined to be a gram negative enteric bacilli having typical *E. coli* reactions in three different media, TSI agar, SIM medium, and Simmons Citrate agar.

A series of *E. coli* bacterial strains were isolated as follows. Experimental strains A-1 through A-10 were isolated from urine specimens at the Indiana University Health Center, the bacterium in each case being nonpathogenic to person from which it was isolated and therefore considered to be a normal flora contaminant from that person's gastrointestinal tract. Strains A-11 through A-20 were similarly isolated from the Bloomington, Indiana, Hospital where, through a long series of biochemical tests, it had been determined that the bacterial strains were lactose negative *Escherichia coli*. Thus, the 20 different strains were isolated from 20 different individuals.

These 20 strains were unable to ferment lactose within 48 hours in TSI agar, EMB agar, and other lactose containing media. Nineteen of these 20 strains were able to produce beta-galactosidase when induced with IPTG. None of the 20 strains had galactoside permease activity (i.e., lactose transporting activity). Cells lacking the ability to accumulate galactosides (such as lactose) do not build up a sufficiently high level of lactose inside the cell to induce the lac operon. When the lac operon is not induced, beta-galactosidase is produced at 1/100 to 1/1000 of the induced level.

Thus, 95% of the lactose negative *E. coli* isolated at the clinical labs were lactose negative only because they were unable to actively transport lactose into the cell. This defect also results in the cell's inability to be induced by lactose and thus the cell appears to be beta-galactosidase negative. IPTG induces the lac operon even in cells that lack galactoside permease activity which results in the production of beta-galactosidase. The incorporation of IPTG into diagnostic media allows the production of beta-galactosidase in galactoside permease negative cells which do not produce beta-galactosidase in a medium containing lactose.

By using media in accordance with this invention, it is possible readily to identify and differentiate Enterobacteriaceae, to determine those that give false indications of lactose negativeness, and to differentiate between lac inducible and lac constitutive bacteria.

I claim:

1. In a diagnostic medium for culturing micro-organisms comprising at least one nutrient, the improvement comprising incorporating therein an amount of isopropyl-beta-D-Thiogalactopyranoside effective to induce the production of beta galactosidase in lactose negative strains of *E. Coli*.

2. An improvement as claimed in claim 1, wherein the isopropyl-beta-D-thiogalactopyranoside is present at a level of about 0.0024-0.01%, by weight.

3. An improved diagnostic medium for use in isolating, identifying, and classifying Enterobacteriaceae comprising at least one nutrient and an amount of isopropyl-beta-D-thiogalactopyranoside effective to induce the production of beta galatosidase in lactose negative strains of *E. coli*.

4. A diagnostic medium, as claimed in claim 3, wherein the isopropyl-beta-D-thiogalactopyranoside is present at a level of about 0.0024-0.01% by weight.

5. A diagnostic medium, as claimed in claim 3, wherein nutrient comprises lactose.

6. An improvement, as claimed in claim 1, wherein the nutrient comprises agar.

7. A method for classifying microorganisms comprising the steps of:
   inoculating the micro-organism onto a diagnostic medium comprising at least one nutrient and an amount of isopropyl-beta-D-thiogalactopyranoside effective to induce the production of beta galactosidase in lactose negative strains of *E. coli;*
   incubating te inoculated medium; and
   assaying the inoculated medium for beta-galactosidease.

8. A method, as claimed in claim 7, wherein the isopropyl-beta-D-thiogalactopyranoside is present in the medium at a level of about 0.0024-0.01% by weight.

9. A method, as claimed in claim 7, wherein the medium is assayed for beta-galactosidase by measuring the degree to which the incubated microorganism hydrolyzes orthonitrophenyl-beta-D-galactopyranoside.

* * * * *